United States Patent
Berger et al.

(10) Patent No.: US 9,395,109 B2
(45) Date of Patent: Jul. 19, 2016

(54) EFFICIENT CHILLER FOR A SUPERCRITICAL FLUID CHROMATOGRAPHY PUMP

(75) Inventors: Terry A. Berger, Englewood, FL (US); Kimber Fogelman, Hockessin, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 490 days.

(21) Appl. No.: 13/699,804

(22) PCT Filed: May 26, 2010

(86) PCT No.: PCT/US2010/036255
§ 371 (c)(1),
(2), (4) Date: Mar. 18, 2014

(87) PCT Pub. No.: WO2011/149456
PCT Pub. Date: Dec. 1, 2011

(65) Prior Publication Data
US 2014/0190183 A1    Jul. 10, 2014

(51) Int. Cl.
*F25B 21/02*    (2006.01)
*F04B 39/06*    (2006.01)
*F04B 53/08*    (2006.01)
*B01D 15/40*    (2006.01)
*G01N 30/32*    (2006.01)

(52) U.S. Cl.
CPC .............. *F25B 21/02* (2013.01); *F04B 39/064* (2013.01); *F04B 53/08* (2013.01); *B01D 15/40* (2013.01); *G01N 2030/326* (2013.01)

(58) Field of Classification Search
CPC ........ F25B 21/02; F04B 39/064; F04B 53/08; B01D 15/40; G01N 2030/326
USPC ........................................................... 62/3.2
See application file for complete search history.

(56) References Cited

U.S. PATENT DOCUMENTS

| | | | |
|---|---|---|---|
| 2,932,953 A * | 4/1960 | Becket | F25B 21/02 136/204 |
| 4,520,305 A * | 5/1985 | Cauchy | F28D 15/0275 136/208 |
| 5,147,538 A | 9/1992 | Wright et al. | |
| 5,180,293 A * | 1/1993 | Hartl | F04B 39/06 417/366 |
| 5,465,581 A * | 11/1995 | Haertl | F04B 15/08 210/198.2 |
| 5,711,155 A * | 1/1998 | DeVilbiss | A61F 7/0085 62/3.3 |
| 6,293,107 B1 * | 9/2001 | Kitagawa | F25B 21/02 62/3.2 |
| 7,083,395 B2 | 8/2006 | Maiefski et al. | |
| 2003/0215341 A1 * | 11/2003 | Maiefski | F04B 9/042 417/313 |
| 2003/0217738 A1 * | 11/2003 | Ryon | F02M 31/20 123/541 |
| 2005/0263176 A1 * | 12/2005 | Yamaguchi | F02G 5/00 136/203 |
| 2006/0130888 A1 * | 6/2006 | Yamaguchi | F01P 3/20 136/205 |
| 2010/0011781 A1 * | 1/2010 | Lents | B64D 13/00 62/3.7 |
| 2010/0050659 A1 * | 3/2010 | Quisenberry | B60H 1/00478 62/3.61 |
| 2010/0058778 A1 * | 3/2010 | Bhatti | F24F 3/1423 62/3.7 |

* cited by examiner

Primary Examiner — Mohammad M Ali (57) ABSTRACT

A system for chilling a pumping system includes a Peltier cooling element, and first and second heat exchangers. The Peltier element is arranged near a pump head of a pump such that the Peltier element and the pump head are in thermal contact, where the Peltier element chills the pump head and a mobile phase flowstream prior to fluid from the mobile phase flowstream entering the pump. The first heat exchanger is attached to the Peltier element, and removes heat from the Peltier element using a circulating fluid. The second heat exchanger cools the circulating fluid, where the Peltier element and the pump head are arranged in an area that is isolated from the second heat exchanger.

21 Claims, 6 Drawing Sheets

EFFICIENT CHILLER FOR A SUPERCRITICAL FLUID CHROMATOGRAPHY PUMP

RELATED APPLICATIONS

The present application is a U.S. national phase application under 35 USC §371(c) of International Application Pub. No. WO/2011/149456 filed on May 26, 2010, naming T. Berger and K. Fogelman as inventors. The entire disclosure of International Application Pub. No. WO/2011/149456 is hereby incorporated by reference in its entirety.

TECHNICAL FIELD

The present invention relates to methods and systems for pumping compressible fluids. More specifically, it relates to pumping compressible fluids in high pressure applications such as high-pressure liquid chromatography (HPLC) or supercritical fluid chromatography (SFC) applications.

BACKGROUND

Industrial pumping takes many forms, all with the general requirement of transporting fluids or slurries through a process stream. Pumps are selected based on the application requirements including head pressure, metering accuracy, temperature, particle tolerance, fluid viscosity, cost, safety, service rate and a variety of other parameters. Pumps can generally be classified in two categories. Positive displacement pumps isolate discrete volumes of the working fluid and force them to move in a controlled direction. Kinetic pumps operate by adding kinetic energy to the system which creates a local increase in fluid velocity. Kinetic energy is converted to potential energy, i.e. pressure, at the pump output.

Figure 1:
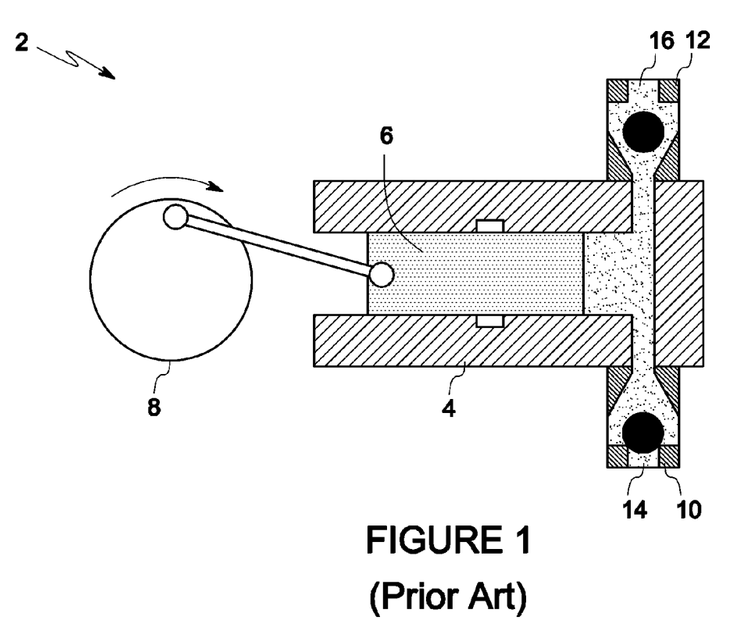
FIG. 1 is a diagram of a conventional simplex reciprocating pump.

Reciprocating pumps, such as pump 2 shown in the diagram of FIG. 1, remain a primary industrial means of pumping fluids when high purity, high pressure (e.g. >100 bar to more than 1000 bar) and high precision (e.g. <1% flow variation) are needed. Reciprocating pumps come in several formats including mechanical and pneumatic piston pumps, and mechanical and hydraulic diaphragm pumps. Such pumps 2 are characterized by having one or more pump heads 4 which transfer fluid between a low pressure input and a higher pressure output. Each pump head 4 contains a means of physically adjusting the internal volume available to the pumped fluid. In operation, each pump head 4 uses a piston 6 driven by a cam 8 that alternately aspirates fluid from the input 10 by increasing the available pump head volume, then dispenses the fluid to the output 12 by decreasing this volume. Most reciprocating pumps are designed to flow in only one direction. Flow direction is controlled by a series of check valves 14, 16 that isolate the pump head from the output pressure during aspiration and from the input pressure during dispensing. The output pressure is generally controlled, not by the pump, but rather by the downstream resistance-to-flow of the process flow stream serviced by the pump.

Reciprocating pumps are characterized by the number of pump heads they utilize. A pump with a single pump head is referred to as a simplex pump. Duplex, Triplex and Quad pumps refer to pumps with two, three and four heads respectively. Two or more pumps heads are required to provide pseudo-continuous flow since one pump head can be delivering while the other is aspirating. However, since the very nature of the movement involves stopping and restarting in opposing motions, reciprocating pumps can only emulate continuous rotary pumps approximately. In general, the greater number of pump heads for a given flow rate, the lower the pulsation of the output stream.

When fluid being pumped by a piston pump is relatively incompressible, these pumps are frequently referred to as metering pumps, since the volumetric flow of the fluid is presumed to match the mechanical volumetric displacement of the piston or diaphragm in the pump head. An example of a metering application of a reciprocating pump is a low pressure syringe pump, in which a glass syringe draws in an aqueous solution and dispenses it very accurately to a downstream reservoir. Under this low pressure use (generally less than 2 bar) the volumetric compression of aqueous solutions is almost immeasurable and thus the presumption of accurate displacement is correct.

When reciprocating pumps are used with very compressible fluids such as permanent gasses, they are frequently called compressors or gas boosters. Gas boosters represent an ideal example of the influence of fluid compressibility on pump performance. In this case, the typical application is to increase the pressure of the gas between the input and output. A fundamental characteristic of gas boosters is the compression ratio. The compression ratio is simply the ratio of the maximum fluid volume a pump head can isolate between its check valves at the peak of its intake stroke to the minimum volume it can reduce to at the end of its delivery stroke. Hence, a compression ratio of 7:1 indicates the total volume at intake is seven times greater than the residual fluid volume at the end of delivery.

Figure 2:
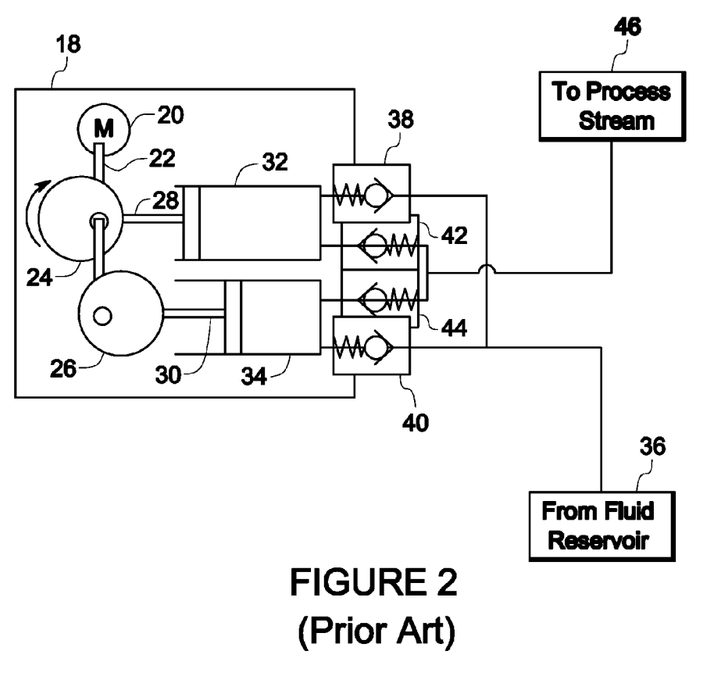
FIG. 2 is a diagram of a conventional duplex reciprocating pump.

FIG. 2 shows the basic components for an HPLC pump of prior art. HPLC pump 18 is an example of an electric cam driven pump. In this case motor 20 rotates shaft 22 to rotate eccentric cams 24 and 26 to provide a reciprocating motion of pistons 28 and 30 contained in pump heads 32 and 34 respectively. As each piston aspirates, fluid is drawn from fluid reservoir 36 through input check valve 38 or 40 respectively. Output check valve 42 or 44 remains sealed during aspiration. During the delivery stroke, input check valve 38 or 40 is shut while output check valve 42 or 44 opens to deliver fluid to process stream 46. The cam drive shown in FIG. 2 is just one example of an HPLC pump. Others would include ball screw drives, pneumatic drives and hydraulic drives coupled to the pistons 28 and 30. Much of the remaining discussion focuses on pumping a fluid using compression compensation of laboratory-type HPLC and SFC type pumps that are similar in design to HPLC pump 18.

Requirements for pumps used in typical laboratory HPLC instruments are very demanding. Pumps must be able to deliver at very high pressures (up to 400 bar for traditional HPLC and as high as 1000 bar for recent ultrahigh performance LC systems). A 2000 bar ultrahigh performance LC system is expected. HPLC pumps must also be able to handle fluids of ultra-high purity without contributing detectable contamination. In addition, for a given flow rate, the volumetric delivery of fluid is expected to remain constant within narrow limits (<1% variation) across the majority of the operational pressure range. Finally, the same pump is also expected to vary flow precisely over at least an order of magnitude of range in periods as short as one minute. This is the result of the need for a technique called gradient elution in which the two solvents controlled by separate pumps are systematically adjusted in relative composition from a weakly to a strongly eluting mixture while maintaining a constant combined flow rate.

Normally, an unmodified high performance liquid chromatography (HPLC) pump would deliver an unknown and varying amount of a compressible fluid under such conditions. As the column head pressure increases during the gradient, a larger percentage of each pump stroke would be used up compressing the fluid instead of delivering flow. With an uncompensated pump, the delivery rate becomes a smaller fraction of the flow setpoint. When a second pump is added to a system to deliver an incompressible fluid under high pressure, its delivery rate is unaffected by the increasing pressure. Subsequently the two pumps deliver inaccurate flow and composition to the mobile phase. As the pressure in the system rises, the total flow drops below its setpoint, but the concentration of the modifier increases beyond the modifier setpoint. The temperature of the compressible fluid in the pump head must be controlled to prevent the delivered mass flow from changing even further.

When compressed, a pumping fluid heats up and attempts to expand. For highly compressible carbon dioxide at outlet pump pressures above 200 bar, a temperature rise of more than ten degrees centigrade is possible within the fluid. The rapid compression of the pumping fluid causes the fluid to heat up and expand and the density to decrease. When heat is transferred to the pump body, the pumped fluid cools and the fluid density increases. Compressibility levels encountered in ultrahigh performance chromatographic systems are very similar to those encountered in supercritical fluid chromatography (SFC) over the last twenty years. In the past, almost all pumps sold to perform SFC or supercritical fluid extraction (SFE) were modified versions of high performance liquid chromatography (HPLC) pumps.

SFC is a separation technique closely related to high performance liquid chromatography (HPLC), except that one of the fluids used in the mobile phase is a liquefied gas. The fluids are generally compressed and are used at pressures above 80-100 atmospheres. The most common fluid in SFC is carbon dioxide but other fluids have sometimes been used. The carbon dioxide is stored in a supply cylinder, as a gas, in equilibrium with a liquid phase, under pressure. Depending on "room temperature", the pressure in the supply cylinder may be approximately 40 to 60 atmospheres. It is much more difficult to pump carbon dioxide than a normal liquid, since its compressibility is very high and it readily expands to a gas at room temperature, unless an external pressure is applied.

SFC uses liquefied $CO_2$ as one of the components of the mobile phase. As a liquefied gas, $CO_2$ must be delivered at high pressure to the pump head in order to remain in the liquid state. This is normally accomplished by connecting a tank containing both liquid and vapor $CO_2$ in thermal equilibrium. A dip tube in communication with the $CO_2$ liquid of the tank is plumbed directly to the pump head, however, the $CO_2$ may become partially or fully vaporized prior to entering the pump head. Thus, pre-conditioning of the $CO_2$ flowstream and pump head becomes essential to proper operation of the SFC or HPLC system. Generally, chilling of the pump head and pre-chilling of the fluid are both necessary to insure that $CO_2$ remains in the liquid state during pump aspiration. Special grades of high purity $CO_2$ are used in SFC to prevent dissolved components of less pure $CO_2$ from affecting the optical clarity of the mobile phase. Mixtures of $CO_2$ and common organic solvents also tend to have higher changes in refractive index than corresponding water: organic solvent mixtures so that small rapid variations in composition are more observable with optical detectors.

When the pump attempts to fill, the pressure in the tube may drop below the pressure in the supply cylinder and some of the fluid may vaporize. The motor on the pump and the associated electronics tend to warm the pump, to above room temperature (i.e., 30-35° C.). If the pump temperature is greater than the supply cylinder temperature, the fluid will further vaporize inside the pump head. Since modern HPLC pumps have relatively low compression ratios they cannot function effectively as gas compressors. The fluid must be present in the pump as a liquid. Modified HPLC pumps must perform both compression and metering of the carbon dioxide to produce accurate flows. HPLC pumps do not normally need to be chilled. However, an SFC pump must be cold enough to not vaporize liquid carbon dioxide entering the pump head (i.e., it must be colder than the supply cylinder. In order to insure the pump head is cold enough to pump liquid carbon dioxide, it is generally cooled to significantly below ambient temperature. Pre-chilling the fluid, before it enters the pump lowers its compressibility.

As mentioned, pumping of liquid $CO_2$ takes special precautions to insure a continuous liquid supply into the pump head. The compressibility of liquid $CO_2$ is also a major factor since it is typically as much as ten fold higher than most of the organic liquids. Further, compression of $CO_2$ between 60 bar (approximate tank pressure) and 400 bar (the maximum system pressure) can raise the fluid temperature more than 25° C. Such a temperature rise dramatically alters the density of the delivered fluid and introduces even more requirements for pump control.

In a pump performing both compression and metering, the actual mass flow delivered by the pump depends on the pump head temperature. To insure accurate and repeatable flow rate, the pump head and carbon dioxide temperature must be both below the temperature of the supply cylinder, and tightly controlled. To perform SFC with pre-existing HPLC pumps, chillers were connected to the pump heads. Hewlett Packard introduced the first commercial SFC in 1982 using a modified 1084 HPLC. The HPLC pumps used were massive, with large electric motors. It was necessary to cool the pump heads to keep the carbon dioxide liquid, and prevent cavitation. The SFC pumps employed a heat exchanger consisting of hollow compartments made of brass, bolted to each pump head. An external, commercial circulating bath pumped a mixture of water/antifreeze through tubing connected to the heat exchangers. The temperature of the circulating bath was set to −20° C. The chilled liquid was circulated through the chambers bolted to the HPLC pump head, by the circulating pump in the bath, chilling the pump heads. In addition, a coil of tubing was placed inside the circulating bath allowing the fluid to be pre-chilled before entering the pump. In spite of all these efforts, the pumps sometimes cavitated, which resulted in inaccurate flow.

HPLC pumps were not intended to be used with vapor phase carbon dioxide. They were used with supply cylinders with "dip" tubes, a tube that extended from the cylinder valve to near the bottom of the cylinder. The liquid layer of carbon dioxide was withdrawn from the cylinder, chilled, and presented to the pumps. Use of the liquid layer from the cylinder eases pumping problems, and decreases the cooling load on the chiller, but exposes the samples to potential contamination in the carbon dioxide. Liquid carbon dioxide can act as a solvent for many relatively non-polar compounds including greases. To avoid contamination, a special grade of carbon dioxide was developed (SFC Grade) that was guaranteed to be pure. This SFC Grade carbon dioxide cost up to 15 times more than many common industrial grades.

Since, in such SFC units, the chiller, the tubing of the circulating bath, the connecting tubing delivering the fluid to the pump head, the heat exchanger on the pump head and the pump head itself, were all below the freezing point of water, humidity in the laboratory air condensed and/or froze on the pump head and tubes. The use of sub-0° C. pump head settings sometimes resulted in large blocks of ice forming on the $CO_2$ pump from ambient humidity in the lab air. This condensation and freezing has no relation to the intended purpose of the chiller and is wasted energy, which forces the use of a much larger circulating chiller than is actually necessary to chill the fluid and pump-head. The size of the external chiller required depends on the relative humidity of the lab air, which can vary greatly throughout a year. Subsequently, the chiller must be sized for the worst case conditions, which is far larger than nominal. Further, some prior solutions to remove the ice formations include isolating pump heads with insulation and blowing hot air onto the iced pump head, which creates even more wasted energy in the ironic situation of air heating of a pump head area that is at the same time being chilled to remove internal heat. Collection and safe removal of the condensate creates an additional undesirable complication. The $CO_2$ delivery pumps are generally fitted with a leak sensor that shuts off the power if a leak (or condensation) is detected. The condensation, although not technically a leak, can trigger the leak sensor.

The ice and condensation problems inspired later SFC pump designers to use pump head temperatures slightly above freezing, such as 5° C. For example, Thar/Waters corporation designers currently use an external chiller connected to the pump heads with large bore tubes, very similar to the design of the original 1084. The Jasco SFC/SFE (Supercritical Extraction System) initially used this approach when introduced in 1985. The Gilson system, introduced in 1992, used this approach. However, operating above freezing only partially solves the problems related to SFC pumps. A chiller mounted on or anywhere around a pump head will still have cold surfaces exposed to humid ambient air, resulting in copious amounts of condensate that robs the chiller of most of its power while creating an unwanted waste stream. The chiller must still be sized to be much larger than actually needed to chill the carbon dioxide and pump head.

Using a separate commercial circulating bath to chill an HPLC pump can make transport and servicing of the individual components difficult and messy. In typical systems, a commercial circulating bath, with dimensions of 2.5 to 5 cubic feet is used, which is connected to a separate pump module with 4-6 feet of ⅜ths to ½ inch OD tubing. Some chillers provide 2500 Watts of cooling (or more). Such circulating baths have their own control electronics and power cable, are bulky, and are expensive. Since previous embodiments chilled the circulating fluid to below room temperature, the connecting tubing had to be heavily insulated, making it extremely thick, and unwieldy, yet excessive condensation on the tubing is still common.

The only other common chiller used in SFC employed Peltier thermoelectric elements directly on the pump head along with finned heat exchangers cooled by forced convection of lab air. With the passage of electric current, one side of the Peltier device becomes cold, directly chilling the pump head, while the other side becomes hot. A fan blows room temperature air through the finned heat exchanger, mounted on the hot side, removing the heat from the heat exchanger. This arrangement eliminates the need for an external chiller, connected to the pump with large bore elastomeric tubing, filled with cold, circulated fluid.

The first SFC pump to use this Peltier configuration was introduced by Hewlett Packard in 1992. In one prior design (Haertle, energy efficient pump)), a heat exchanger was embedded in the pump head to pre-chill the liquid carbon dioxide before it entered the pump, while the Peltier device lowered the pump head temperature to 4-5° C. In yet another embodiment by Haertle, there was a counter flow heat exchanger used that contacted the incoming carbon dioxide with the carbon dioxide exiting the pump to pre-chill the fluid and attempt to minimize the amount of cooling power needed. The finned heat exchanger and a high volume fan were mounted directly on top of the pump head. The need to have large volumes of air contact the heat exchanger on one face of the Peltier device made it difficult to isolate the other cold face of the Peltier device from the large volumes of moist air, since they were only separated by ≈⅛th inch. Water vapor from the laboratory air condensed on the pump head, robbing it of efficiency. The Peltier elements had to be over-sized to provide many times the cooling power actually needed to pump $CO_2$, in order to cope with the unwanted condensation. Extensive insulation tended to minimize this condensation, but blocked easy access to the pump head for routine maintenance.

Another significant problem is how to maintain a pump that has problems with chiller designs described above. All pumps require routine maintenance, such as periodic replacement of check valves and the main seals on pistons. Typically, a large finned heat sink is mounted on the front of the pump which completely blocks access to the pump head for routine maintenance. The need to remove the chiller for access, complicates maintenance. Jasco, Selerity, and SSI all pursued similar approaches with the heat exchanger mounted directly on the pump head, but left out the heat exchangers in the Haertle patents. Thar/Waters has announced a similar approach in upcoming products. All these approaches require excessively large Peltier devices or elements, and complicate routine maintenance.

A further problem is that although often powerful, all previous condensers used in SFC could not guarantee that the fluid in the pump was actually a liquid or that the mass flow delivered was accurate.

SUMMARY

The present invention, as described in the various embodiments, represents an improved cooling device and/or system) and method, or chiller and method of chilling, a pump head for use in a supercritical fluid chromatography (SFC) system. The method and system of the embodiments may be used on any type of pumping system that requires cooling of the pump head. Exemplary applications include liquid chromatography systems, HPLC systems, ultra-HPLC systems, SFC systems, and industrial and commercial systems used to pump gasses.

In one exemplary application, two pumps are used in series; one to compress the fluid to near the working pressure and the other to precisely meter the flow. Separating the two tasks means that the condenser temperature becomes relatively unimportant, since its only job is to allow the booster pump to increase the pressure of the fluid regardless of the flow rate. Here, the chiller is an integral part of the first pump, called a booster pump, since it guarantees liquefaction of the fluid, allowing the pump to boost pressure, and is mounted in the same enclosure as the pump.

The present invention solves numerous problems with prior designs. For example, it liquefies vapor phase carbon dioxide, thereby allowing the use of low grade $CO_2$ which significantly lowers operating costs. It maintains a high range of cooling by minimizing the condensation of atmospheric water vapor. It minimizes energy consumption by minimizing the condensation of atmospheric water vapor. It eases control requirements, since the temperature is irrelevant as it only needs to be below approximately 9° C. It dramatically reduces the physical size of the chiller proximal to the pump head by relocating the final heat exchange to a remote location, yet allows easy service and access to the pump head for maintenance by leaving the pump heads completely exposed.

In an embodiment, the chiller assembly, the circulating system and the pump are all mounted on a single, small, self-contained drawer occupying less than about 1 cubic foot that mounts into a mainframe. All electrical connections are internal and made through a single connector. Removing several screws, two tubes, and unplugging the electrical connector allows easy removal of the drawer from the mainframe for service.

The embodiments use both a Peltier element and a circulating fluid, cooled by a fan blowing ambient lab air through a high surface area liquid radiator. However, here the circulating fluid is always in contact with the hot side of the Peltier element. Thus, the "cooling" flow is always above ambient temperature, and is not likely to cause any loss of efficiency by condensation of water out of the lab air.

Carbon dioxide ($CO_2$) is supplied from a room temperature steel or aluminum cylinder as a gas. Using the vapor phase, or gaseous state, effectively distills the carbon dioxide just before use, leaving most contaminants behind in the cylinder. Using the gaseous state dramatically decreases the cost of the fluid. Typical operation at 3 ml/min for 200-10 hr days/year saves approximately $6000/year, compared to SFC Grade $CO_2$. However, using the gaseous state requires the chiller to be powerful enough to always recondense the fluid to a liquid phase, or liquid state, before use. Older chillers, particularly those based on the Peltier principle, were not specifically designed to condense the gaseous state and cool the pump head.

The chiller condenses the gas to a liquid and delivers it to the pressure booster pump. The booster pump raises the pressure of incoming carbon dioxide to almost match the output pressure of a downstream metering pump. In this way the booster, acting as a pressure source, does all the compression on the fluid while the second pump in series meters carbon dioxide flow.

Since the function of the first pump is simply to raise the pressure of the fluid, and the second pump exclusively meters the flow, any effect of supply cylinder temperature and pressure and booster pump head temperature on mass flow rate is eliminated. The actual temperature of the chiller is immaterial as long as the fluid exists as a liquid in the booster, although lower temperature allows the pump to deliver the same required mass with fewer strokes. By separating the functions of compression and metering to two different pumps, flow noise is greatly reduced. These are major advantages over all previous SFC pumping schemes.

The act of compression from 60 bar to 400 bar can raise the temperature of carbon dioxide as much as 25° C. Provision is also made in the present invention to pass the fluid exiting the pump through an additional heat exchanger to remove the heat of compression from the fluid before it is transferred to the metering pump. In one embodiment a second flow plate is included in the same chiller plate for this function. In a second embodiment, the chiller temperature is held low enough that at the highest adiabatic compression rates, the $CO_2$ will remain significantly near the desired delivery temperature (e.g. room temperature). This allows facile adjustment of the flow temperature as needed.

Several specific target applications include pumping of liquids in ultrahigh performance chromatographic systems and pumping of liquefied gasses such as $CO_2$ in SFC systems. Moreover, by separating the compression and metering functions, the metering step occurs over a very small range of pressure and temperature. As a result, by measuring pressure and temperature of the metering step to determine fluid density and adjusting volumetric flow accordingly, true mass flow control of the pump can be obtained. Finally, the invention facilitates applications of continuous pump designs such as gear and lobe pumps that offer superior pulse free delivery to reciprocating pumps but have limited ability to generate high differential pressures under the required conditions of purity.

DETAILED DESCRIPTION

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

Figure 3:
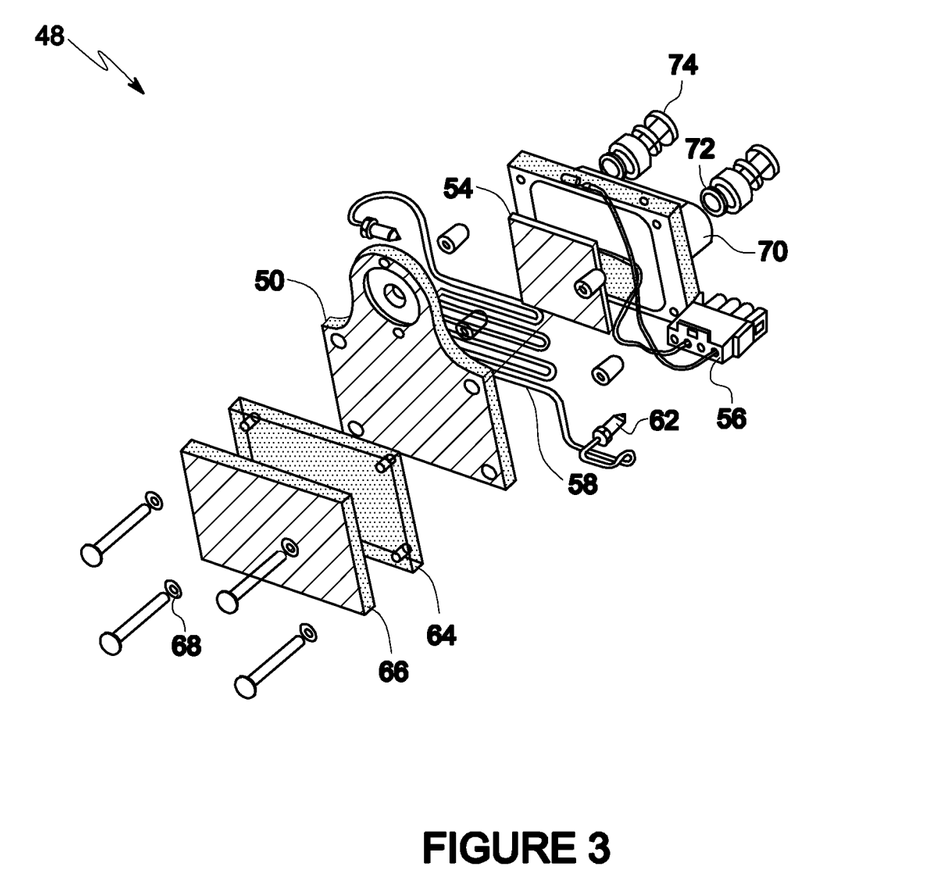
FIG. 3 is a diagram of and exploded view of a representative embodiment of the chiller assembly.
Figures 4, 5:
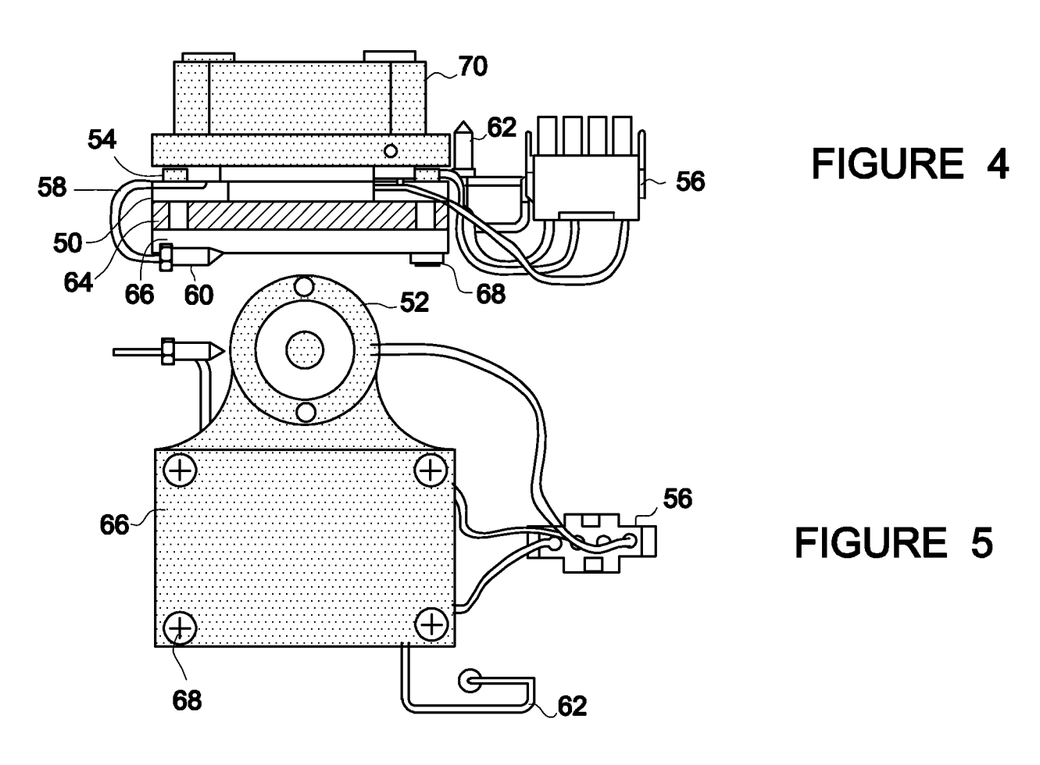
FIG. 4 is a diagram of the side view of the representative embodiment of the chiller assembly.
FIG. 5 a diagram of the front view of the assembled chiller assembly.

Referring to FIGS. 3, 4 and 5, a schematic illustration of a representative pump head chiller assembly 48 is displayed. A cold plate or chiller plate 50 is attached to a Peltier element 54 with associated electrical connectors 56. The chiller plate 50 is formed out of copper but could be aluminum or other appropriate materials. Chiller plate 50 is mounted near or behind a pump head through a plate extension 52. In one embodiment, the chiller plate 50 is mounted perpendicular to the pumping axis onto a housing frame via a support plate 66. A labyrinth of bent or serpentine stainless steel tubing 58 (hereinafter "tubing") is embedded in or located on or near the chiller plate 50. The tubing 58 has an inlet 62 and an outlet 60. A brazed cooler block 70 of a first heat exchanger mounts to the Peltier element 54 using an appropriate mounting technique such as seating compound such as ceramique thermal seating compound. The Peltier element 54 is positioned approximately to the center of cooler block 70. Inlet 72 and outlet 74 adapters for cooler block 70 connect tubing for fluid flowstreams to and from a second heat exchanger.

A spacer plate 64 constructed of plastic or other insulating material is located between the support plate 66 and the chiller plate 50. Spacer plate 64 thermally isolates the chiller plate 50 from radiative heating. The support plate 66 and the cooler block 70, on either side of chiller plate 50 also serve as structural support for pump head chiller assembly 48. The pump head chiller assembly 48 is held together via screws 68 or other appropriate attaching elements.

Referring again to chiller plate 50, the side of the chiller plate 50 against which the Peltier element 54 would be pressed comprises the tubing 58 that is pressed into channels within chiller plate 50. A thermal compound is applied to the tubing 58 and the chiller plate 50 to ensure good thermal contact with both the aluminum (or copper) metal in the chiller plate 50 and the stainless steel of the tubing 58. Carbon dioxide gas enters the tubing 58 at inlet 62 and is pre-chilled and liquefied before it reaches the base of the pump via outlet 60. Accordingly, the chiller plate 50 and the tubing 58 may be part of a prechiller assembly. A temperature sensor is located in the chiller plate 50 immediately behind the pump head. Thus the chiller plate 50 can maintain good thermal contact with and cool both a pump head and the tubing 58 for the flowstream. The cooler block 70 is a liquid heat exchanger, and may be constructed of copper clad materials, coated stainless steel, or brass. Pre-chilling the carbon dioxide flowstream via thermal contact between the chiller plate 50 and the pump head enhances the ability to maintain the carbon dioxide fluid in a liquid state while in the pump during compression and delivery.

The chiller plate 50 nominally operates near about negative 10 degrees Celsius (°C.), for example. The $CO_2$ flowstream in gaseous state enters the tubing 58 at the inlet 62, turns to liquid state in the chilled tubing 58, exits at the outlet 60, and enters into the pump head as chilled liquid. The present embodiments for the pump head chiller assembly 48 operate not only at sub-ambient temperatures, but also at a sub-freezing point of water. Conventional pump designs, whether liquid or Peltier chilled, have always avoided going below 0 degrees C. because of the problem of building up of ice onto the components, as described above. The present invention isolates the heat exchange components of the cooler block 70, except for the inlet 72 and outlet 74 adaptors, within a vapor tight compartment 78 (hereinafter "compartment", FIGS. 6-8) that prevents infiltration of atmospheric moisture. The flat face of the cooler block 70 is mounted in direct contact with the warm side (or "hot" side) of the Peltier element 54. Circulation of coolant within the cooler block 70 maintains the Peltier "hot" surface at just a few degrees Celsius above room temperature. Since efficiency of the Peltier element 54 depends on the delta T (change in temperature) that currently exists across the Peltier element 54, keeping the temperature of the warm side as low as possible allows lower working temperatures on the cold side of the Peltier element 54.

The cold side of the Peltier element 54 functions to transfer heat away from the chiller plate 50, from the gas-state $CO_2$ entering the tubing 58 to convert the gas-state $CO_2$ to liquid-state $CO_2$ in the tubing 58, and from the back of the pump head 80 (FIGS. 7 and 8) via the plate extension 52 to carry away the adiabatic heat of compression, as pressure in the system reaches up to 400 bar. Temperature fluctuations depend on workloads for the system. With no load, temperatures reach in a range of about negative 15 to negative 20 degrees C., with standard operation loads temperatures reach a range of about negative 12 to negative 5 degrees C., and with very high loads and with very high ambient temperatures, the system can operate at about +5 to 6 degrees C. above zero and still meet the demands of the pump which is operating/drawing at about 5 ml/minute, for example. A typical operating range is well outside the marginal zone for operation.

Figure 6:
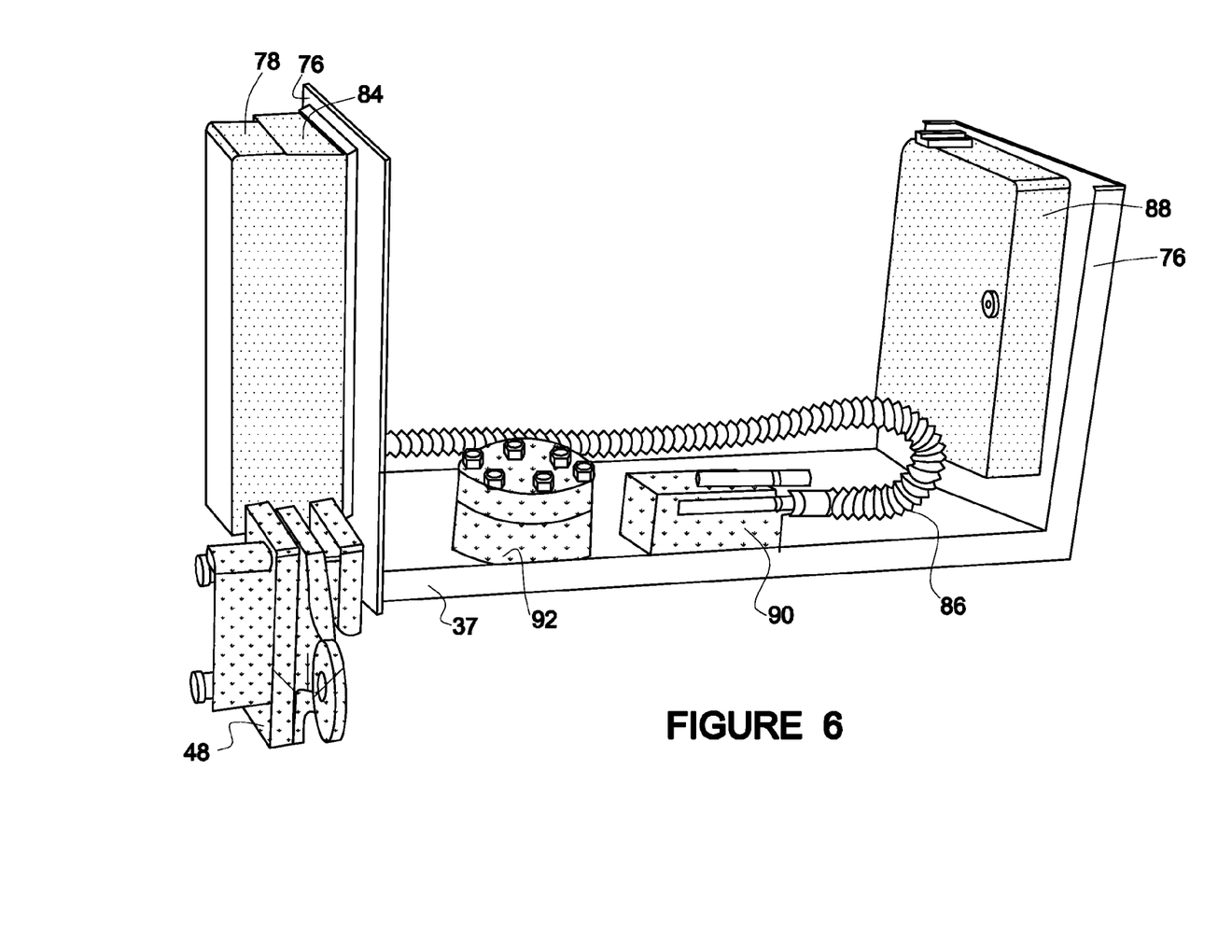
FIG. 6 is a right profile view of the assembled pump drawer showing the radiator, circulator pump, and enclosed chiller assembly and pump head.
Figure 7:
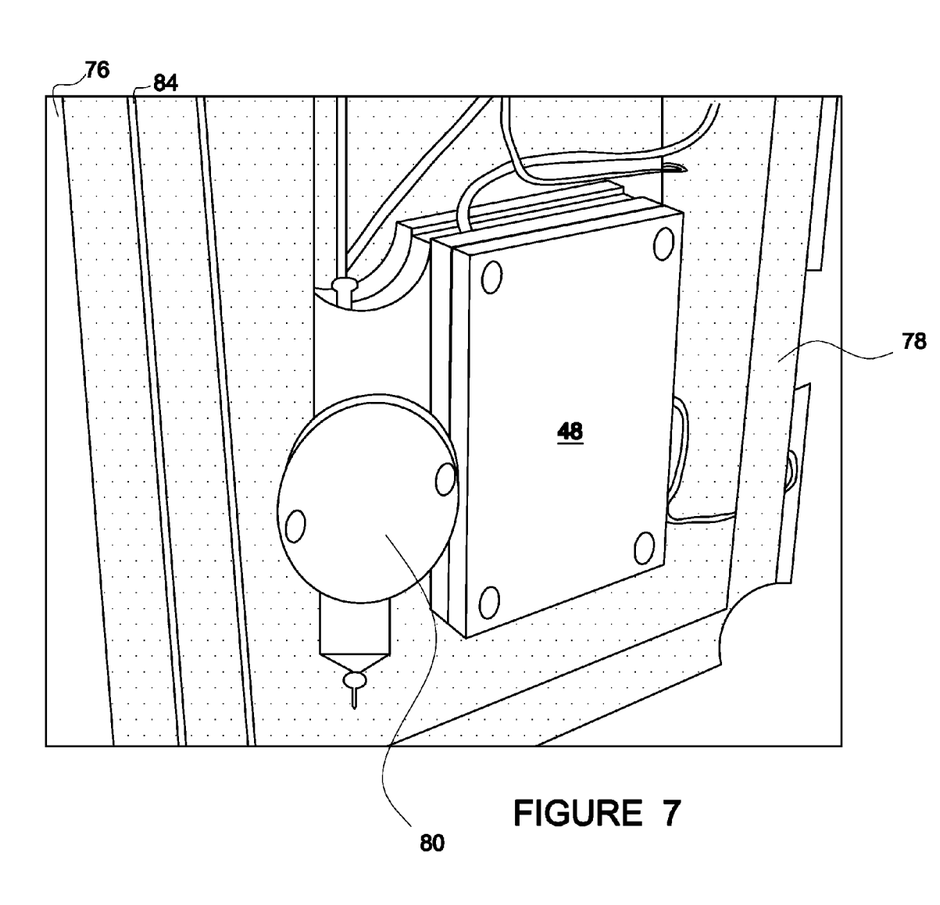
FIG. 7 is a front view of the pump drawer showing the chiller assembly mounted behind the pump head within a vapor tight enclosure.
Figure 8:
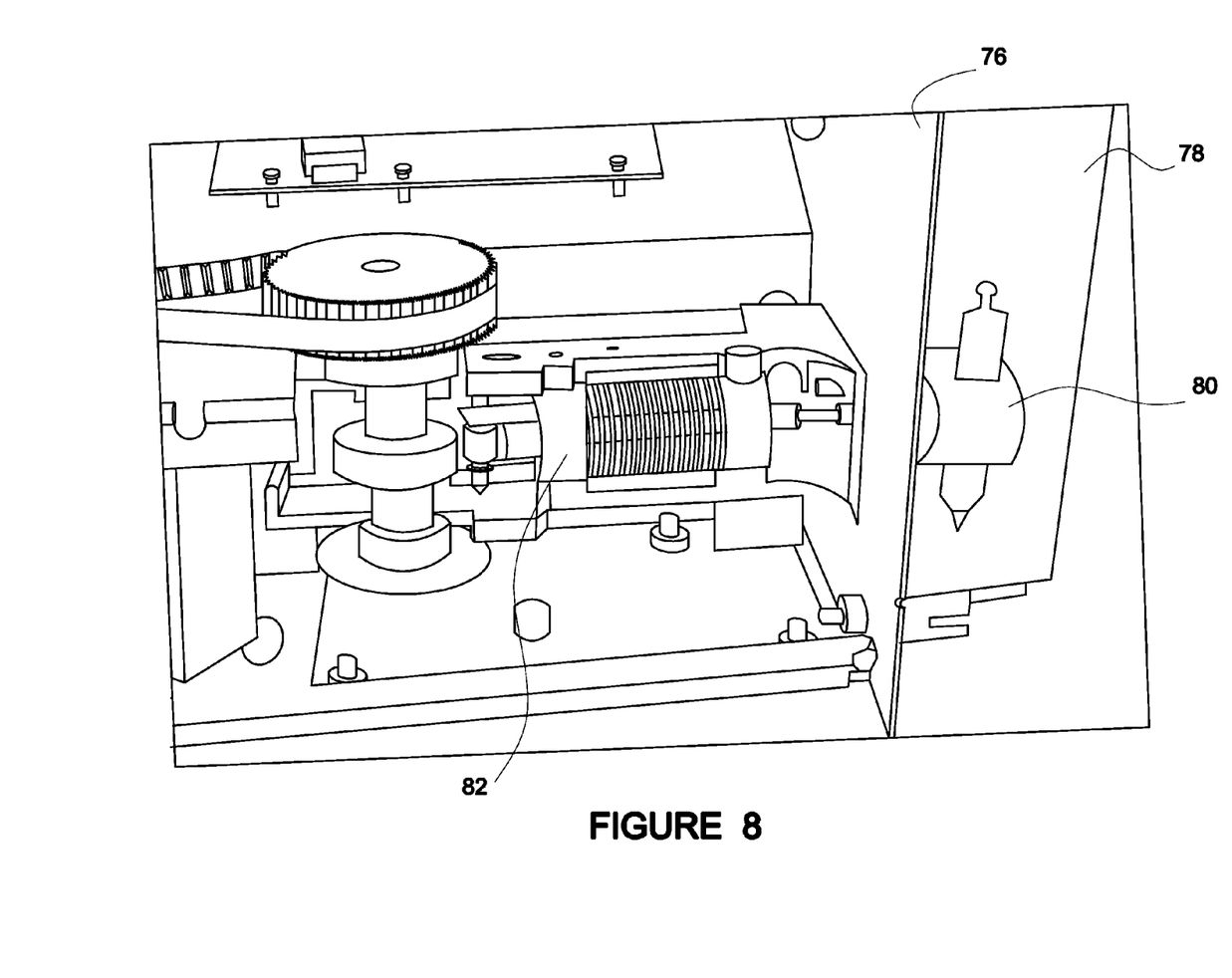
FIG. 8 is a left side profile of the pump drawer showing the pump drive mechanism positioned outside the vapor tight enclosure.

FIGS. 6, 7, and 8 illustrate embodiments for a pump head chiller assembly 48 mounted to a pump frame housing 76. The pump head chiller assembly 48 is clamped between the pump head 80 and an insulating spacer 94, all of which are placed inside of the sealed compartment 78, which is enclosed and insulated. Using the pump head chiller assembly 48 in such an arrangement, the pump head 80 of pump 82 is exposed and can be removed for servicing without loosening the chiller plate 50.

To seal the interior components of the compartment 78, there is a foam vapor barrier provided by foam backing 84. The embodiment uses a specially designed insulating spacer 94 positioned behind the chiller plate extension 52 both to seal to against the foam backing 84 and provide pressurized contact between the chiller plate extension 52 and the pump head 80. In addition, the back plate of the cooler block 70, is designed so that when the pump head 80 is secured, the inlet and outlet ports of the cooler block 70 protrude through the foam backing 84 and connect to heat exchanger low pressure tubing 86. The compartment 78, which may be plastic, excludes air, and thus moisture, from interior components, and the foam backing 84 is closed cell foam, which excludes water. Thus, the compartment 78 excludes nearly all ambient water vapor from reaching the chiller plate 50 and the pump head 80. Air inside the compartment 78 has no, or virtually no, air exchange with external ambient air. Ambient air containing water vapor can only contact the chiller plate 50 and the pump head 80 when a front panel or cover of the compartment 78 is removed for servicing or maintaining the components. Once the pump head chiller assembly 48 begins operation, any moisture trapped in the air within the compartment 78 will be deposited as a thin film of ice on the chiller plate 50 and the pump head 80 but is not replaced. While the compartment 78 remains sealed, no additional condensation can occur on the pump head chiller assembly 48 or the pump head 80, thus no additional loss of efficiency is encountered. Liquid condensation resulting in accumulation of water on and around the pump head chiller assembly 48 is also avoided.

As shown in FIG. 7, removing the front panel of the compartment 78 exposes the pump head 80. The check valve holders are directly exposed, allowing normal replacement of the check valves for inlet and outlet flow to and from the pump 82. The pump head 80 can be removed by loosening two exposed nuts, exactly as is done with the pump head chiller assembly 48, allowing easy replacement of the pump main piston seal. The check valves and pump seals can be replaced for routine maintenance without removing the pump head chiller assembly 48.

As shown in FIG. 6, the system further comprises the second heat exchanger, which may include a radiator 88 and fan, installed distal to the pump head chiller assembly 48 in the pump frame housing 76, and configured to provide ambient cooling (i.e., heat exchange) of the circulating coolant. The cooler block 70 of the liquid first heat exchanger is configured to remove heat from the hot side of the Peltier element 54 (FIGS. 3 and 4). The inlet and outlet side of the cooler block 70 penetrates the rear wall of the compartment 78, through the pump frame housing 76 so that inlet and outlet flowstreams of the circulating fluid (coolant) in the low pressure tubing 86 can be attached. A heat exchanger circulating fluid such as a propylene glycol/water mixture is circulated through the cooler block 70 by a small centrifugal pump 90, such as a commercial liquid circulating pump of the type used to cool computers. The heat exchanger is hermetically sealed to prevent water from leaking outside of its components. The heat exchanger fluid is then pumped through a high surface area, car-like, radiator 88 located some distance from the pump 82. Room temperature air is blown through the radiator 88 by the large, dedicated fan. The air flow from the fan does not strike the chiller plate 50 or the pump head 80 due to the compartment 78. There can be no condensation on the low pressure tubing 86 for the circulating fluid, or the radiator 88 or the small centrifugal pump 90 since they are all warmer than room temperature. Due to the efficiency of how water carries away heat, the heat exchanger fluid does not vary its temperature significantly, and in some embodiments remains in the range of about 28 to 30 degrees C. during its entire operation. An alternative to water cooling is using air. However more power is generally used in a Peltier device with air cooling which may bring the air in the heat exchange system up to about 35 or 40 degrees C. and therefore maintaining a low temperature of about zero or negative 10 degrees C. at the pump head 80 would be much less efficient. Water cooling helps maintain the cooling effects of the Peltier device so that it shifts down the effective range of average cooling temperature and thereby the cooling capacity of the embodiment.

Regarding gaseous entry into the system, $CO_2$ in gaseous state enters from a remote supply through an on/off valve, passes temperature and pressure sensors, and flows through a tube to a bulkhead fitting through the pump frame housing 76 into the compartment 78. Once in the compartment 78, the flowline enters at inlet 62 into the tubing 58 in the front of the chiller plate 50, then the bottom of the tubing 58 goes into an entry tube to the pump head 80. Because of the negative 10 degrees C. nominal temperature of chiller plate 50, $CO_2$ rapidly liquefies prior to reaching the outlet 60 of the tubing 58, when it enters the pump head 80. Thus, $CO_2$ is a gas when it enters the heat exchanger/Peltier tubing 58 and exits as a liquid ready for compression.

Within the chiller plate 50, there is a limited volume of the tubing 58, for example, about 40 to 45 cm of tubing, so it can provide a few hundred microliters of total volume in the tubing 58. An alternative embodiment for a chiller plate 50/tubing 58 arrangement is to use a high surface-area plate and expose the plate to a cavity or volume. A larger volume with a high surface area plate, such as with fins, placed against a Peltier unit, creates a larger volume of gas in the liquid, which can be siphoned out of the bottom of the unit. Another alternative embodiment is to coil the tubing continuously, instead of a serpentine arrangement. A further alternative uses two Peltier units instead of just one for a chiller arrangement to extend the volume that can be liquefied.

After compression at the pump head 80, the flowstream of compressed $CO_2$ flows through a tube in the compartment 78 to a bulk-head fitting though the pump frame housing 76, and enters pulse dampener 92. The pulse dampener 92 may be a 25-mL empty volume, for example, located inside the pump frame housing 76. After passing a final pressure sensor, the $CO_2$ flowstream is ready for transfer to a metering pump or other downstream system process.

Overall, the pump head chiller assembly 48 and the compartment 78 creates a very efficient chilling system over prior systems. Smaller Peltier cooling units may be used on SFC systems than have been used in prior systems, yet the smaller units provide colder temperatures for cooling the pump heads and allow unequivocal condensation of adequate vapor to meet all the liquid needs of the system.

An additional, high value use of the chiller plate 50 is as a condensing unit to liquefy compressible fluids supplied to the booster in vapor form. Such capability creates a much broader variety of sources of the working fluid. A premier example is liquefying $CO_2$ from a lower purity source such as a beverage grade $CO_2$ reservoir. By sampling from the gas state of the tank rather than the liquid state, the $CO_2$ is actually distilled, which removes nonvolatile impurities from the working fluid. Purity of the $CO_2$ working fluid can be elevated well above the purity of traditional high purity $CO_2$ grades such as SFC or SFE grades costing at least an order of magnitude more. By sampling from a high pressure cylinder, the $CO_2$ pressure is already very near the room temperature gas-liquid equilibrium pressure. As a result, only the heat of vaporization needs to be removed (a few watts of cooling per gram) to form liquid $CO_2$. From this point, lowering the temperature further, e.g. below 10° C., gives sufficient margin to prevent cavitation of the liquid $CO_2$ during the aspiration portion of the piston stroke.

Another advantage of delivering vapor $CO_2$ to the pump is the dramatically reduced cost of distributing a modest pressure gas stream throughout a laboratory or process site as opposed to delivering high pressure liquefied gas. If the pre-chiller is capable of cooling $CO_2$ below −20 degrees C. the pressures of $CO_2$ available to most dewar cylinders and bulk tank installations become available as sources. Hence a high power prechiller can truly lower the operating cost of the $CO_2$ supply as well as allow its safe transport though low pressure piping within a facility. The economics are largely driven by the relative cost of bulk beverage grade $CO_2$ at less than $0.10 per pound compared to SFC grade $CO_2$ at more than $7.00 per pound—a 70-fold increase.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A pump head chiller assembly for chilling a pump head of a pump, the pump head chiller assembly comprising:
   mobile phase tubing comprising a mobile phase inlet, a mobile phase outlet configured to fluidly communicate with the pump head, and a multi-turn tubing section between the mobile phase inlet and the mobile phase outlet, wherein the mobile phase tubing is configured to flow a mobile phase through the mobile phase tubing and toward the pump head;
   a Peltier element comprising a cool side and an opposing hot side;
   a chiller plate arranged on the cool side, wherein:
      the mobile phase tubing is interposed between and in thermal contact with the cool side and the chiller plate, such that the Peltier element and the chiller plate are configured to pre-chill the mobile phase, including a compressible fluid thereof, in the mobile phase tubing;
      the cool side is in thermal contact with the chiller plate such that the Peltier element removes heat from the chiller plate; and
      the chiller plate is configured for mounting in thermal contact with the pump head such that the chiller plate removes heat from the pump head; and
   a first heat exchanger comprising a cooler block arranged on the hot side and configured to remove heat from the Peltier element by circulating a coolant through the cooler block.

2. The pump head chiller assembly of claim 1, wherein the mobile phase tubing is embedded in, or disposed in a channel of, the chiller plate.

3. The pump head chiller assembly of claim 1, wherein the compressible fluid comprises carbon dioxide.

4. The pump head chiller assembly of claim 3, wherein the mobile phase inlet is configured to receive the carbon dioxide as gaseous carbon dioxide, and the Peltier element and the chiller plate are configured to pre-chill the gaseous carbon dioxide sufficiently to liquefy the gaseous carbon dioxide such that liquefied carbon dioxide exits the mobile phase outlet.

5. The pump head chiller assembly of claim 1, wherein the chiller plate comprises a plate extension configured to mount the chiller plate to the pump head and to carry away adiabatic heat of compression from the pump head.

6. The pump head chiller assembly of claim 1, wherein the Peltier element is attached to the chiller plate, or to the cooler block, or to both the chiller plate and the cooler block.

7. The pump head chiller assembly of claim 1, comprising a fluid-sealed, thermally insulated compartment enclosing the Peltier element, the mobile phase tubing, the chiller plate, and the cooler block, wherein:
 the compartment is configured to enclose the pump head while allowing the mobile phase to exit the pump head to an output line external to the compartment; and
 the compartment is configured to contain the cooler block while allowing the coolant to be circulated between the cooler block and a second heat exchanger disposed external to the compartment and configured to cool the coolant.

8. A pump head chilling system for chilling a pump head of a pump, the pump head chilling system comprising:
 the pump head chiller assembly of claim 1, wherein the cooler block comprises a cooler block inlet and a cooler block outlet; and
 a second heat exchanger communicating with the cooler block inlet and the cooler block outlet and configured to cool the coolant.

9. A pumping system, comprising:
 the pump head chiller assembly of claim 1; and
 the pump, comprising the pump head, wherein:
 the pump head is configured to receive the flow of pre-chilled mobile phase from the mobile phase outlet; and
 at least a portion of the chiller plate is mounted adjacent to the pump head.

10. The pumping system of claim 9, comprising a carbon dioxide gas supply fluidly communicating with the mobile phase inlet, wherein the mobile phase inlet is configured to receive a flow of carbon dioxide gas from the carbon dioxide gas supply, and the Peltier element and the chiller plate are configured to pre-chill the carbon dioxide gas sufficiently to liquefy the carbon dioxide gas such that liquefied carbon dioxide exits the mobile phase outlet and enters the pump head.

11. The pumping system of claim 10, wherein the carbon dioxide gas supply comprises a reservoir containing a liquid layer of liquefied carbon dioxide and a head space of carbon dioxide gas separate from the liquid layer, and the mobile phase inlet is in fluid communication with the head space.

12. The pumping system of claim 9, wherein:
 the pump is a first pump and the pump head is a first pump head;
 the pumping system further comprises a second pump comprising a second pump head;
 the first pump is configured for pressurizing the pre-chilled mobile phase and delivering the pressurized mobile phase to the second pump head; and
 the second pump is configured for metering the flow of the mobile phase to an outlet of the pumping system.

13. A pump head chilling system for chilling a pump head of a pump, the system comprising:
 mobile phase tubing comprising a mobile phase inlet, a mobile phase outlet configured to fluidly communicate with the pump head, and a multi-turn tubing section between the mobile phase inlet and the mobile phase outlet, wherein the mobile phase tubing is configured to flow a mobile phase through the mobile phase tubing and toward the pump head;
 a Peltier element comprising a cool side and an opposing hot side and configured for mounting near the pump head such that the cool side removes heat from the pump head, wherein the mobile phase tubing is in thermal contact with the cool side such that the Peltier element is configured to pre-chill the mobile phase, including a compressible fluid thereof, in the mobile phase tubing;
 a first heat exchanger arranged on the hot side and configured to remove heat from the Peltier cooling element by circulating a coolant;
 a second heat exchanger configured to cool the coolant; and
 a fluid-sealed, thermally insulated compartment enclosing the Peltier element, the mobile phase tubing, and the first heat exchanger, wherein:
 the compartment is configured to enclose the pump head while allowing the mobile phase to exit the pump head to an output line external to the compartment;
 the compartment is configured to contain the first heat exchanger while allowing the coolant to be circulated between the first heat exchanger and the second heat exchanger; and
 the second heat exchanger disposed external to the compartment such that the Peltier element and the mobile phase tubing are thermally isolated from the second heat exchanger.

14. The pump head chilling system of claim 13, comprising a chiller plate arranged on the cool side, wherein:
 the mobile phase tubing is interposed between and in thermal contact with the cool side and the chiller plate, such that the Peltier element and the chiller plate are configured to pre-chill the mobile phase in the mobile phase tubing;
 the cool side is in thermal contact with the chiller plate such that the Peltier element removes heat from the chiller plate; and
 the chiller plate is configured for mounting in thermal contact with the pump head such that the chiller plate removes heat from the pump head.

15. The pump head chilling system of claim 13, wherein the compressible fluid comprises carbon dioxide.

16. The pump head chilling system of claim 15, wherein the mobile phase inlet is configured to receive the carbon dioxide as gaseous carbon dioxide, and the Peltier element is configured to pre-chill the gaseous carbon dioxide sufficiently to liquefy the gaseous carbon dioxide such that liquefied carbon dioxide exits the mobile phase outlet.

17. The pump head chilling system of claim 13, comprising a configuration selected from the group consisting of:
 the first heat exchanger is configured to maintain the hot side at a few degrees Celsius above room temperature;
 the second heat exchanger is disposed at a distance from the pump head chiller assembly, and further comprising low-pressure tubing interconnected between the second heat exchanger and the first heat exchanger;
 the first heat exchanger and the second heat exchanger are configured to operate above ambient temperature;
 the second heat exchanger comprises an ambient-cooled radiator, or an ambient-cooled radiator and a fan configured to direct air to the ambient-cooled radiator; and
 a combination of two or more of the foregoing.

18. A pumping system, comprising:
the pump head chilling system of claim 13; and
the pump, comprising the pump head, wherein the pump head is disposed in the compartment and is configured to receive the flow of pre-chilled mobile phase from the mobile phase outlet.

19. The pumping system of claim 18, comprising a carbon dioxide gas supply fluidly communicating with the mobile phase inlet, wherein the mobile phase inlet is configured to receive a flow of carbon dioxide gas from the carbon dioxide gas supply, and the Peltier element is configured to pre-chill the carbon dioxide gas sufficiently to liquefy the carbon dioxide gas such that liquefied carbon dioxide exits the mobile phase outlet and enters the pump head.

20. The pumping system of claim 19, wherein the carbon dioxide gas supply comprises a reservoir containing a liquid layer of liquefied carbon dioxide and a head space of carbon dioxide gas separate from the liquid layer, and the mobile phase inlet is in fluid communication with the head space.

21. The pumping system of claim 18, wherein:
the pump is a first pump and the pump head is a first pump head;
the pumping system further comprises a second pump comprising a second pump head;
the first pump is configured for pressurizing the pre-chilled mobile phase and delivering the pressurized mobile phase to the second pump head; and
the second pump is configured for metering the flow of the mobile phase to an outlet of the pumping system.

\* \* \* \* \*